(12) United States Patent
Kert

(10) Patent No.: US 7,665,991 B1
(45) Date of Patent: Feb. 23, 2010

(54) ENDODONTIC OBTURATOR

(75) Inventor: Jimmie Kert, Vaerloese (DK)

(73) Assignee: CMS Dental ApS, Copenhagen (DK)

( * ) Notice: Subject to any disclaimer, the term of this patent is extended or adjusted under 35 U.S.C. 154(b) by 122 days.

(21) Appl. No.: 11/439,622

(22) Filed: May 23, 2006

(51) Int. Cl.
*A61C 5/02* (2006.01)

(52) U.S. Cl. ............. 433/224; 433/81; 433/83; 433/102

(58) Field of Classification Search ........... 433/81, 433/102, 222.1, 224, 83
See application file for complete search history.

(56) References Cited

U.S. PATENT DOCUMENTS

| | | | | |
|---|---|---|---|---|
| 4,681,545 A | * | 7/1987 | Lapcevic | 433/224 |
| 5,051,093 A | * | 9/1991 | Fitzmorris | 433/224 |
| 5,275,562 A | * | 1/1994 | McSpadden | 433/224 |
| 5,882,196 A | * | 3/1999 | Kert | 433/81 |
| 6,010,335 A | * | 1/2000 | Kert | 433/81 |
| 6,254,389 B1 | * | 7/2001 | Seghatol | 433/215 |
| 7,090,499 B1 | * | 8/2006 | Mays et al. | 433/224 |

* cited by examiner

*Primary Examiner*—Cris L Rodriguez
*Assistant Examiner*—Hao D Mai
(74) *Attorney, Agent, or Firm*—Susan L. Crockett, Esq.; Niky Economy Syrengelas, Esq.; Crockett & Crockett

(57) ABSTRACT

An endodontic obturator for filling an endodontically prepared root canal of a tooth. The endodontic obturator includes an elongated shaft of having a proximate portion and a distal portion. The proximate portion has a handle portion connected thereto or is suitable for being releasably connected to a handle portion. A layer of filler material is coated about the shaft. The filler material has a low operating temperature at which it becomes plasticized or partially molten. The filler material in the layer disposed close to the distal end can have a higher viscosity at the operating temperate than the filler material close to the distal end.

10 Claims, 5 Drawing Sheets

ENDODONTIC OBTURATOR

FIELD OF THE INVENTIONS

The present invention relates to endodontic obturators for use in filling an endodontically prepared root canal of a tooth, especially endodontic obturators that include an elongated shaft of a flexible material surrounded along a part of its length by a filler body of plastic or thermoplastic material.

BACKGROUND OF THE INVENTIONS

Known obturators have a tapered shaft with a round or oval cross-sectional shape and come in various diameter sizes. After properly cleaning and shaping the root canal, the correct obturator size is determined by using size verifiers with uncoated cores and with different diameters. The diameters of the size verifiers usually correspond to the shaft diameters of coated obturators. A loose fit is essential to provide clearance for allowing surplus gutta-percha material to flow back. A too tight fit may prevent the obturator from reaching the required depth. The obturator is to be inserted with the tip of the obturator reaching the apex of the canal.

The filler body is typically gutta percha, compounds of gutta percha and polymer materials or a similar material with the desirable characteristic to function as a root canal filler. At ambient temperature the filler material is relatively rigid. Before the obturator with the gutta-percha filler is applied to the root canal, the filler material is heated over an open flame or in an oven to an operating temperature at which the filler material becomes semi-molten or plasticized, whereupon the obturator is inserted in the root canal to obtain a three-dimensional filling thereof. The obturator is inserted by using a mild pressure to the working distance and not moved anymore, i.e. the filling is realized with a single insertion. The handle or excess part of the shaft is removed by any suitable technique that applies little or no force to the obturator. This method results in good apical seal and can be performed relatively fast, which is of advantage to both dentist and patient and reduces the risk of wetting or contaminating the root canal.

It is highly desired that the canal is filled as completely as possible. The latter is relatively easy to accomplish if the root canal is regularly shaped and the preparation of the canal has the proper smooth and tapered form. However, the root canal is often irregularly shaped due to resorption during an infection of the channel. Resorption causes the walls of the root canal to dissolve and form fissures and recesses that are difficult to fill. It is therefore possible that the root canal widens again in an area close to the apex. The recesses, fissures and widening apex areas make it very difficult with conventional obturators to obtain a complete fill, since the molten or plasticized gutta percha does not build up a pressure of significant magnitude when it is inserted into the root canal (the gutta percha can flow back out of the root canal at relatively low pressures because there is no provision to block or pressurize the open end of the tooth).

Attempts to solve this problem have been made in the past. U.S. Pat. No. 5,083,923 discloses a method of obturating an extirpated root canal utilizing two types of filler material, one type of which is in the form of a gutta-percha point and the other type of which is a thermoplasticized gutta-percha having a melting temperature of about 15 to 20° C. less than the melting temperature of the gutta-percha point. The steps of the method include the introducing of an initial amount of thermoplasticized gutta percha in a heated and softened condition into the root canal so that the initial amount fills the bottom of the canal. A gutta-percha point is then positioned within the root canal and another amount of thermoplasticized gutta-percha is introduced in a heated and softened condition into the canal. The thermoplasticized gutta-percha is then manipulated into contact with the portion of the gutta-percha point positioned within the root canal so that the gutta-percha point is mixed with the thermoplasticized gutta-percha and worked against the wall until all the gutta-percha is compacted within the root canal. The mixing of the gutta-percha point with the thermoplasticized gutta-percha is performed by applying rotary and reciprocal motions with an instrument like a rotary root canal file. Additional amounts of thermoplasticized gutta-percha are introduced and manipulated into contact with additional gutta-percha points as necessary to fill the complete root canal with a core of filler material. A certain pressure on the semi molten gutta-percha is achieved with this method. However, a disadvantage associated with this method is the fact that the gutta percha filling needs to be machined for some time, and that the process has to be repeated several times in order to fill the complete canal, i.e. it is a time consuming procedure.

Conventional filler material has an operating range between 110 and 130° C. at which it becomes plasticized and is ready for insertion into the prepared root canal.

This relatively high temperature has several disadvantages, such as exposure of the tooth material surrounding the root canal to high temperatures, and the risk of burning due to inadvertent contact of the patient and/or the dental practitioner with the hot obturator or with the oven.

SUMMARY

The devices and methods described below provide a method and an obturator that allow a fast and complete 3-dimensional filling of a root canal, even if the root canal is irregularly shaped. An obturator is provided with a cover of gutta percha filler material with a relatively low viscosity at the distal end of the cover and a higher viscosity at the proximal end of the cover. Viscosity of the distal and proximal end of the cover is controlled by new formulations of gutta percha. The filler material may be provided in segments of differing viscosity, or in single segment having a continuously variable viscosity. The desired viscosity may be achieved in significantly lower operating temperature using the new formulations of the gutta percha used for the obturator cover.

BRIEF DESCRIPTION OF THE DRAWINGS

In the following detailed portion of the present description, the invention will be explained in more detail with reference to the exemplary embodiments shown in the drawings, in which.

DETAILED DESCRIPTION OF THE INVENTIONS

Figure 1:
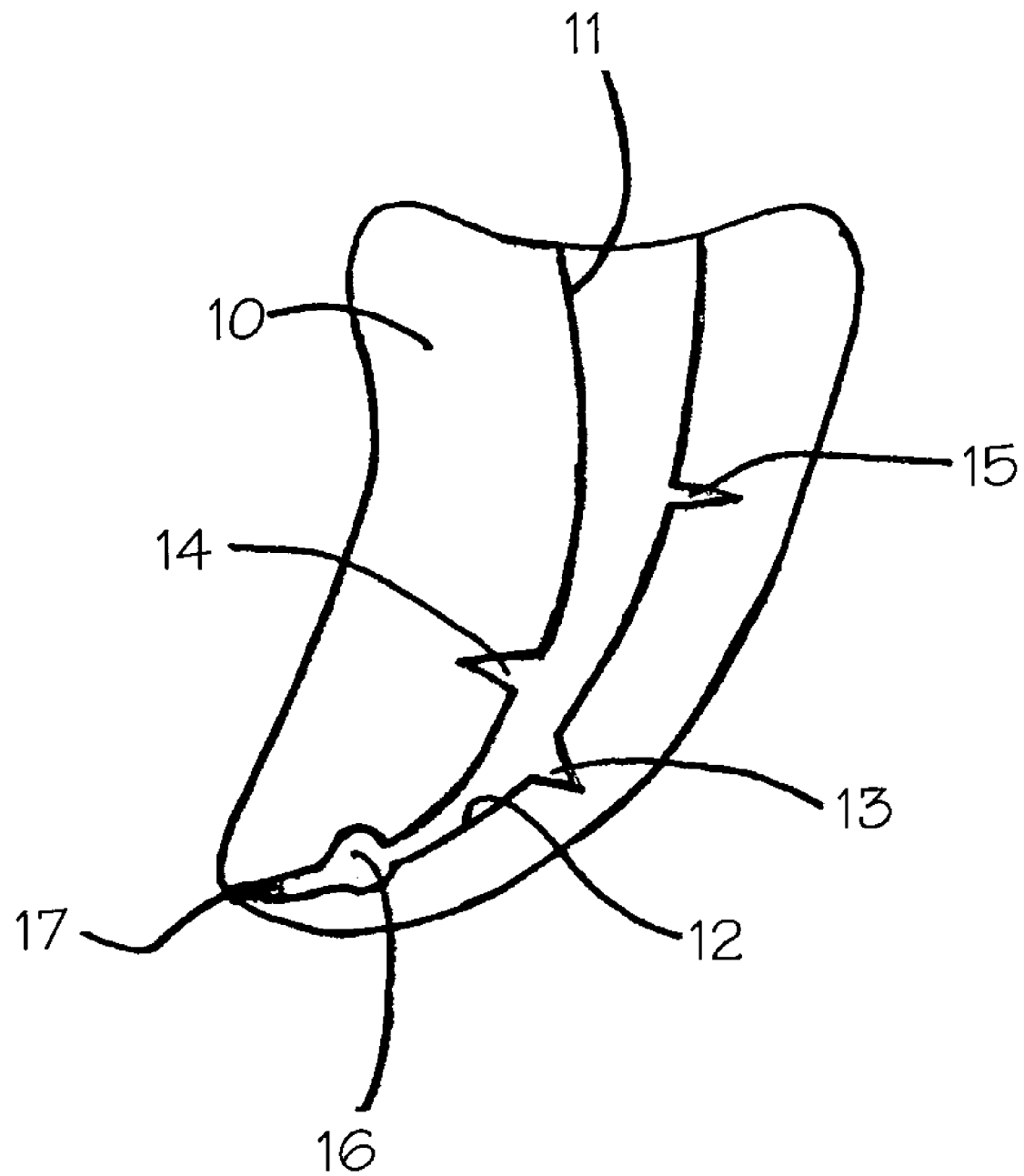
FIG. 1 is a cross-sectional view of a tooth having an extirpated root canal prepared for filling in accordance with an embodiment of a method of the present invention.

Turning now to the drawings in greater detail, there is illustrated in FIG. 1 a tooth 10 having a root canal 11 which has been endodontically prepared (extirpated) in preparation for an obturating (filling) process in accordance with an embodiment of a method of the present invention. The root canal 11 has been prepared in accordance with well-known procedures which remove dead or damaged tissue from the canal 11 in order to provide a smoothly tapering space 12 for accepting filler material inserted and compacted therein. In the depicted tooth 10, there are illustrated fissures 13, 14, 15 defined within the wall of the root canal 11 and a widening 16 of the canal towards the apex 17, which are usually difficult to fill by conventional obturating processes. As will be apparent herein, by inserting an obturator, which is coated with two gutta-percha materials having different melting or plasticizing temperatures or having different dynamic viscosities at the working temperature, into the root canal 11, the entire space of the root canal 11, the fissures 13, 14, 15 defined along the root canal wall and the widening 16 towards the apex 17 are completely filled with a thermoplastic endodontic material. Simultaneously, an excellent coronal seal and seal at the apex 17 are achieved.

Typically, the composition of the thermoplastic material comprises gutta-percha and a number of filler materials. When the term gutta-percha is mentioned hereafter this term is also to cover composites containing gutta-percha.

Both the method and the obturator of the invention utilize, according to an embodiment of the invention, two classes of filler material with different dynamic viscosities at temperatures within an operating range. As used herein, the term "operating range" refers to the temperatures at which the filler material melts from a solid, relatively firm condition to a softened, fluid-like condition possessing little resistance to forces which may tend to deform the material and which is capable of easily conforming in shape to the shape of a container within which the material may be held. Conventionally, the operating range has been between approximately 110 and 130° C. When modified as described below, the lower limit of the range may be lowered to approximately 60° C.

It follows that one class, hereafter referred to as the first class, of the two classes of filler materials discussed herein possesses a viscosity which is lower than that of the other class, hereafter referred to as the second class, of the two classes of filler materials, but both may originate from a similar material state.

For example, gutta-percha in its material state, which in an embodiment of the present invention may be used in the composition of the first and second class filler materials, is known to possess a melting or plasticizing temperature of about 93° C. A gutta-percha form having a lower melting or plasticizing temperature may be achieved by heating of the gutta-percha to an elevated temperature and subsequently cooling the gutta-percha at a controlled rate. For example, an amorphous gutta-percha composition containing primarily an "alpha" crystalline form of gutta-percha when in an untreated state may experience a change during treatment so that at the end of treatment, a gutta-percha composition contains primarily a "beta" crystalline form of gutta-percha having a lower plasticizing temperature.

The second class of gutta-percha material may be a thermoplasticized gutta-percha having a viscosity at temperatures within the operating range that is approximately 50% or more higher than the viscosity of the first class of gutta-percha material at temperatures within the operating range.

Compositions found to be well suited for both the first class and second class filler contain polycaprolactone, gutta percha plus other filler materials.

Example I

Example of composition for obtaining approximately 2200 Poise at 75° C.:

approximately 7% by weight polycaprolactone type P767,
approximately 30% by weight (raw) gutta-percha,
approximately 25% by weight barium sulphate,
approximately 25% by weight zinc oxide,
approximately 5% by weight titanium dioxide,
approximately 6% by weight paraffin wax, and
approximately 2% antioxidants, pigments and other additives.

Example II

Example of composition for obtaining approximately 4200 Poise at 75° C.:

approximately 7% by weight polycaprolactone type P767
approximately 33% by weight (raw) gutta-percha,
approximately 25% by weight barium sulphate,
approximately 25% by weight zinc oxide,
approximately 5% by weight titanium dioxide,
approximately 3% by weight paraffin wax, and
approximately 2% antioxidants, pigments and other additives.

The gutta-percha is preferably of the beta type (heat treated to reduce the melting temperature).

The dynamic viscosity can be changed by varying the type of polycaprolactone, e.g. by using polycaprolactone with a lower dynamic viscosity to obtain a filler material with a lower dynamic viscosity. Alternatively, the viscosity of the filler material can be reduced by increasing the paraffin wax content and vice versa.

Various types of polycaprolactone are commercially available from the Dow Chemical Company under the product designations "Tone PCL 767 polymer", "Tone PCL 787 polymer" and "Tone PCL 757 polymer".

It should be understood that an endodontic obturator according to the principles of the present invention may be obtained by use of any suitably formed obturator body having a shaft of a flexible material and having a tapered distal end about which the filler material is coated.

Figure 2:
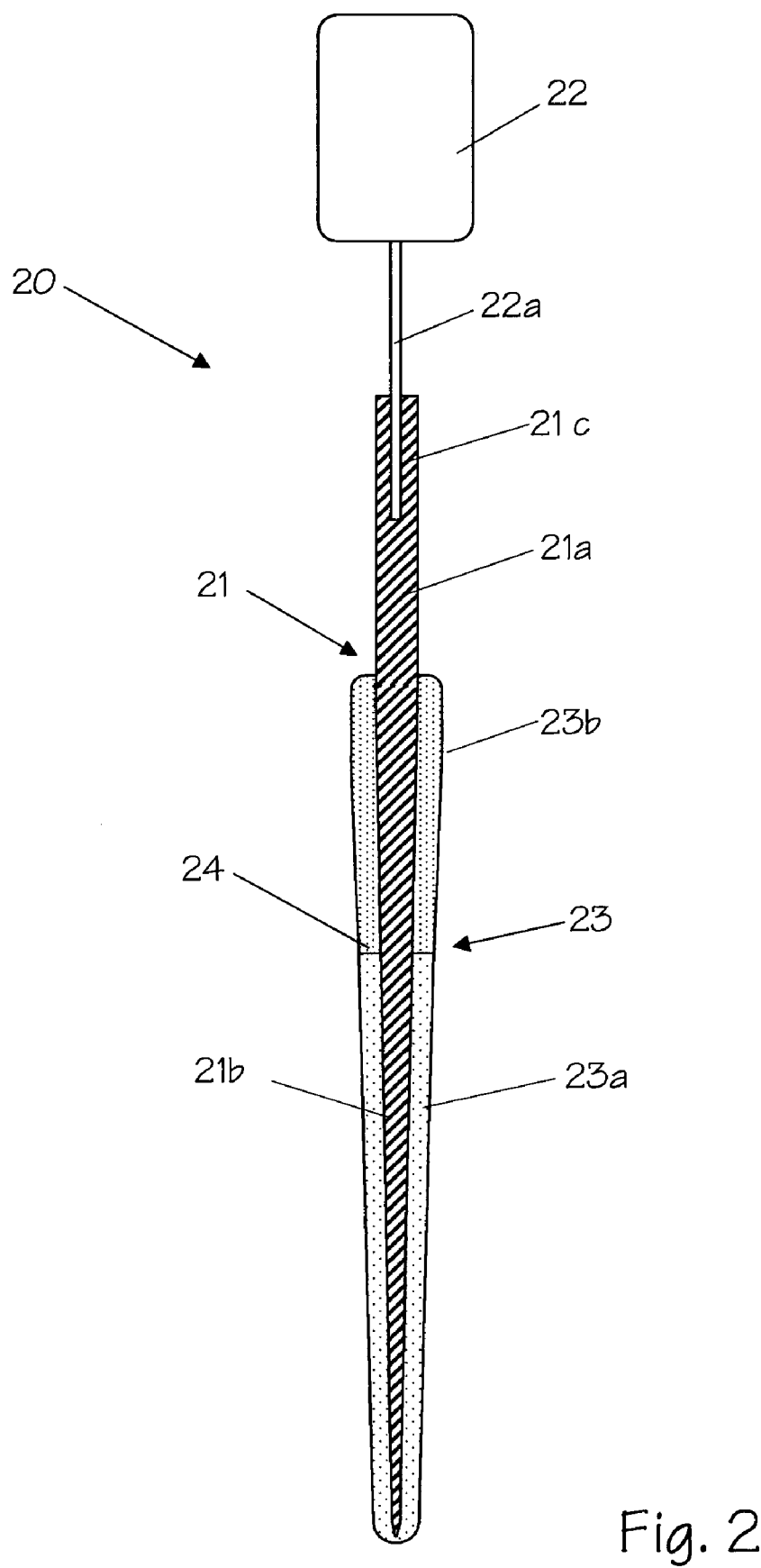
FIG. 2 shows a first embodiment of an endodontic obturator according to the present invention.

Referring to FIG. 2, there is shown a first embodiment of an endodontic obturator according to the present invention, which is generally denoted as 20. The obturator 20 has an elongated shaft 21 with a distal portion 21b and a proximal portion 21a with a handle portion 21c. A handle 22 is connected to the handle portion 21c. The handle 22 may be releasably connected to the handle portion 21c. The distal portion 21b of the shaft 21 has at least a part being tapered to the distal end. The handle 22 is made e.g. from some suitable plastic material and the insertion rod 22a is made e.g. from carbon steel. The shaft is made of a material that is sufficiently soft, or can be made sufficiently soft, so as to make it possible to remove the insertion rod 22a from the shaft portion 21c, when the latter has been placed in its final position in a root canal of a tooth (not shown). Persons with knowledge of plastic materials will know how to choose the correct material for the shaft 21 according to requirements.

A layer of filler material 23 is coated about at least part of the tapered distal portion 21b of the shaft. The layer of filler material 23 is divided in a first portion 23a extending from the distal end of the shaft 21 to an intermediate point or area 24 along the tapered part of the shaft 21 and a second portion 23b extending from the intermediate point or area 24 towards the proximal portion 21a of the shaft.

The first portion 23a of the filler material 23 may be made of a thermoplastic filler material of the above described first class, and has a viscosity at temperatures within the operating range which is higher than that of the second portion 23b of the filler material 23, which second portion 23b may be made of a thermoplastic filler material of the above described second class. The handle 22 may be made e.g. from a suitable plastic material, and the shaft 21 may be made of a biocompatible material such a thermoplastic polymer or a mixture of thermoplastic polymers.

It is within an embodiment of the invention that the viscosity at temperatures within the operating range of the material in the second portion 23b is more than approximately 50% higher than the viscosity at temperatures within the operating range of the material in the first portion 23a.

An example of a suitable selection for the viscosity at temperatures within the operating range is approximately 4200 Poise for the material in the second portion 23b and approximately 2200 Poise for the material in the first portion 23a. Materials with other dynamic viscosities at the operating temperature can be achieved by varying the paraffin wax content and/or by varying the type of polycaprolactone.

It should be understood that when having different viscosities of the filler materials in the first and second portions, 23a and 23b respectively, then the melting of plasticizing temperatures of the filler materials will also be different.

It is also within an embodiment of the present invention that the filler material of the first portion 23a has a color which is different to the color of the filler material of the second portion 23b. The color difference allows dental practitioners to readily recognize obturators that are provided with two different classes of filler material.

Figure 3:
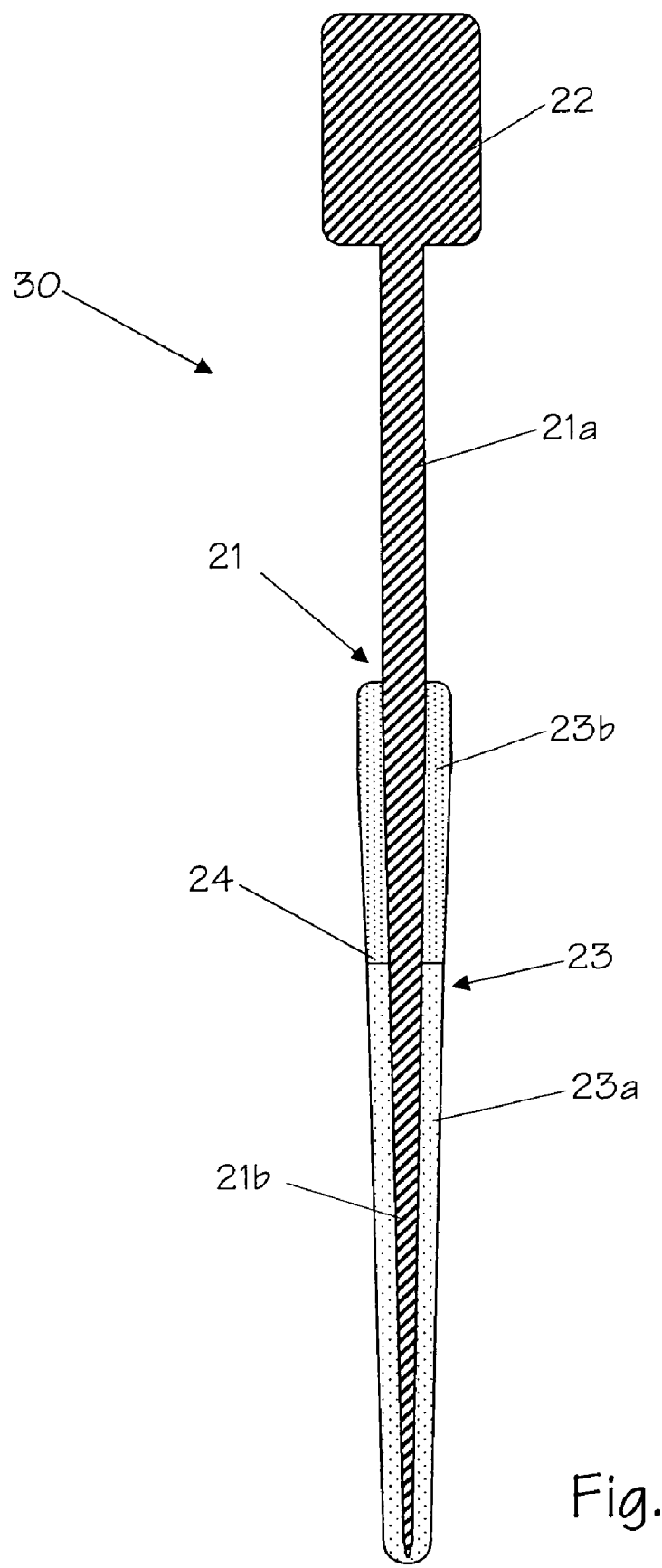
FIG. 3 shows a second embodiment of an endodontic obturator according to the present invention, FIGS. 4a,b,c illustrate obturating of an extirpated root canal by use of an endodontic obturator according to the present invention.

Referring to FIG. 3, there is shown a second embodiment of an endodontic obturator according to the present invention, which is generally denoted as 30. The endodontic obturator shown in FIG. 3 is substantially identical to the obturator according to the embodiment illustrated by FIG. 2, except that the handle 22 is an integral part of the shaft.

In practice, the endodontic obturator 20, of the present invention may be used in the following manner:

When the root canal 11 has been prepared, the layer of filler material 23 is heated to a temperature where it is sufficiently soft to adapt itself to the walls of the root canal 11, i.e. to a temperature at which substantially all the filler material 23 is melted or plasticized. From here the obturator 20 is inserted in the root canal 11 with the distal end of the layer of filler material 23 leading. During the insertion, the obturator is held and moved by means of the handle 22.

When using the obturator 20 of FIG. 2, after the layer of filler material 23 has been placed in its final position in the root canal 11, and sufficient time has elapsed to allow it to cure or set, the handle 22 is removed and the excess part of the shaft 21 is separated, e.g. by cutting the excess part of the shaft 21.

When using the obturator 30 of FIG. 3, then when the layer of filler material 23 has been placed in its final position in the root canal 11, and sufficient time has elapsed to allow it to cure or set, the excess portion of the shaft including the handle part 22 is removed by severing.

The shaft 21 of the obturator 20 of FIG. 2 is made of suitable tissue-friendly materials.

The dimensions of the shaft 21, and the layer of filler material 23 may be varied according to need.

It should be understood that when obturating an extirpated root canal by use of an endodontic obturator according to the principles of the present invention, where the first portion 23a of the filler material in the layer disposed close to the distal end of the obturator has a lower dynamic viscosity than the second portion 23b of the filler material disposed more distant from the distant end of the obturator, that when the obturator with the pre-heated layer of filler material 23 is inserted in the root canal and exercised by means of the handle 22 then the first portion 23a of the filler material has a plunger effect on the second portion 23b of the filler material, thereby causing the pressure at the apex end 17 of the tooth to increase so that a more complete (three-dimensional) filling of the root canal 11 with fissures 13, 14, 15 and widening 16 is obtained when compared to the prior art endodontic obturators.

Figure 4A:
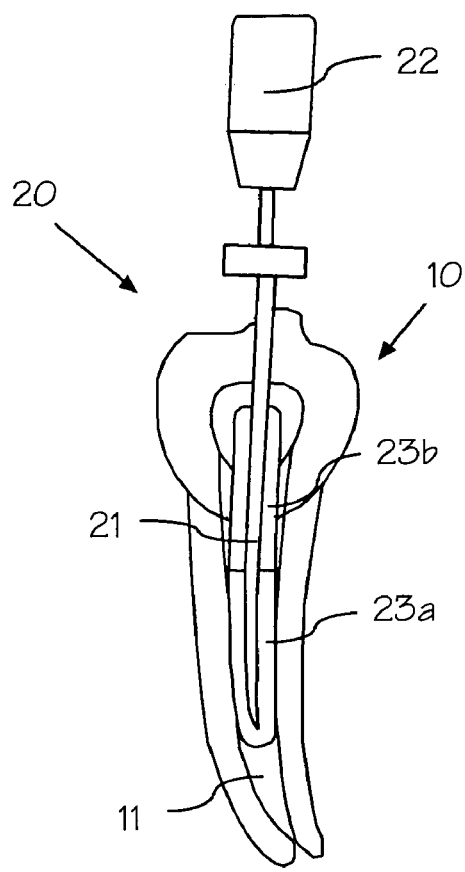
Figure 4B:
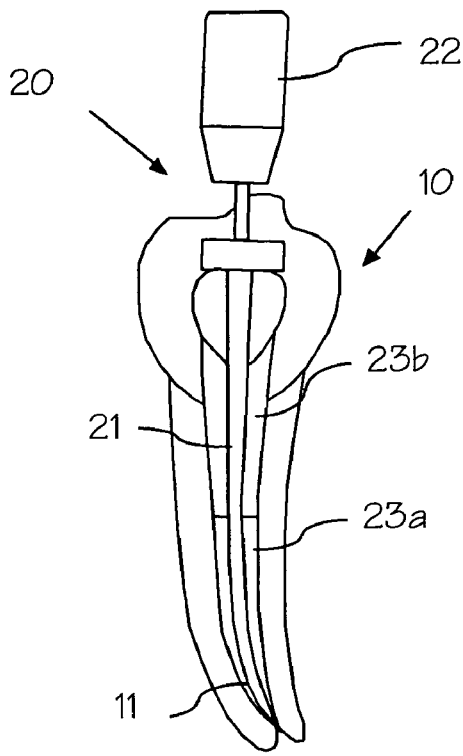
Figure 4C:
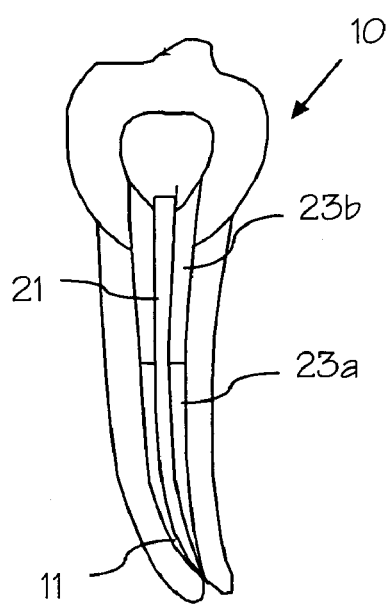

The insertion of an obturator according to the present invention in an extirpated root canal is illustrated in FIGS. 4a,b,c. Here, an obturator substantially similar to the obturator 20 of FIG. 2 is used. In FIG. 4a the obturator 20 is partly inserted in the root canal 11 with the filler material 23a having the lower viscosity leading, and with the filler material 23b with the higher viscosity being closest to the handle 22, whereby the higher viscosity filler material 23b results in a plunger effect during the insertion operation, in which the obturator 20 is moved by means of the handle 22. In FIG. 4b the obturator 20 is fully inserted and the root canal 11 is filled by the filling material 23a, 23b. In FIG. 4c the filler material 23a, 23b has cured and the handle 22 and the excess part of the shaft 21 have been removed.

The above embodiments describe a two-class division of the filler material. However, it will be readily understood that the difference in viscosity can be distributed along the length of the filler layer in more than one step or even gradually (from a low viscosity at the distal end to the high viscosity at the proximate end) in order to obtain the desired plunger effect of the uppermost portion of the layer of filler material.

Figure 5:
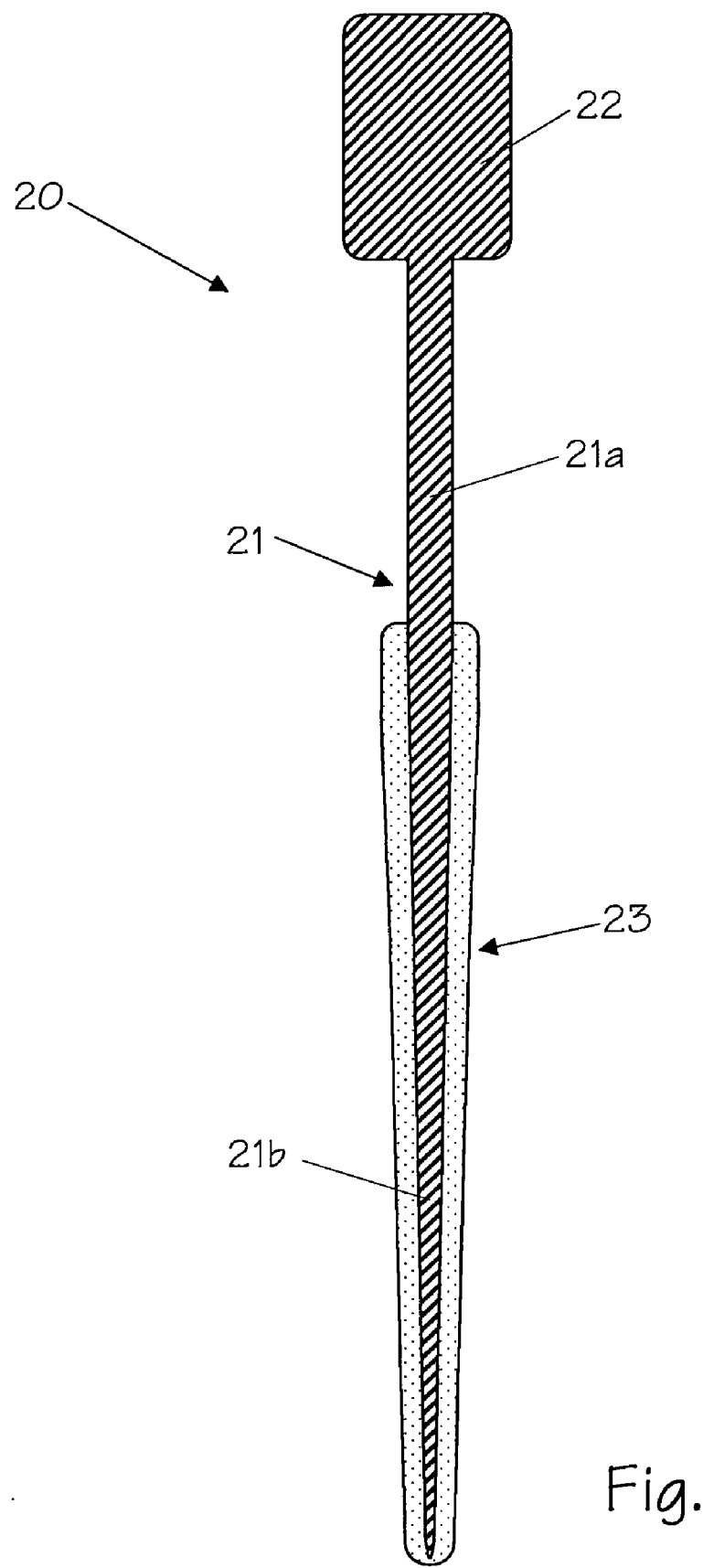
FIG. 5 shows a third embodiment of an endodontic obturator according to the present invention.

Referring to FIG. 5 there is shown a third embodiment of an endodontic obturator 20. The obturator according to the third embodiment is substantially identical to the obturator of the second embodiment except that the filler layer 23 is substantially homogenous so that the dynamic viscosity of the filler material is substantially the same along the length of the shaft 21. The thermoplastic filler layer becomes substantially molten or plasticized at temperatures below 110° C. and has therefore an operation range between 65 and 110° C., preferably between 70 and 80° C. Within the operating range the filler material will have a viscosity below 4000 Poise, preferably below 3600 Poise.

Filler material compositions according to example 1 and example 2 above are suitable for use with the endodontic obturator according to the third embodiment.

The use of the endodontic obturator according to the third embodiment is substantially identical to the use described with reference to the first and second embodiments, except that the plunger effect does not occur.

Although the present invention has been described in detail for purpose of illustration, it is understood that such detail is solely for that purpose, and variations can be made therein by those skilled in the art without departing from the scope of the invention.

I claim:

1. An endodontic obturator for filling an endodontically prepared root canal of a tooth, said endodontic obturator comprising:
    an elongated shaft of a flexible material, said shaft having a distal end, said shaft further having a proximal portion and a distal portion, said distal portion further comprising a tapered part;
    a layer of filler material coated about the distal portion of the shaft said filler material characterized by a dynamic viscosity at a temperature within an operating range;
    wherein the dynamic viscosity of a portion of the layer of filler material near the distal end of the shaft is lower than the dynamic viscosity of a portion of the layer of filler material disposed towards the proximal portion of the shaft when the filler material is heated to a temperature within the operating range;
    wherein the layer of filler material is divided into a distinct first and second portions wherein the first portion extends from the distal end of the shaft to an intermediate point along the tapered part of the shaft and a second portion extends from the intermediate point towards the proximate portion of the shaft, whereby the filler material in the second portion has a higher dynamic viscosity than the filler material in the first portion.

2. An endodontic obturator according to claim 1, wherein the dynamic viscosity in the second portion is more than approximately 50% higher than the dynamic viscosity in the first portion.

3. An endodontic obturator according to claim 1, wherein the filler material of the first portion has a color which is different than the color of the filler material of the second portion.

4. An endodontic obturator according to claim 1, wherein the filler material has a composition comprising gutta-percha and/or polycaprolactone (PCL).

5. A method of obturating an extirpated root canal comprising the steps of:
    providing an endodontic obturator with an elongated shaft of a flexible material, said shaft having a distal end, said shaft further having a proximal portion and a distal portion, said distal portion further comprising a tapered part;
    a layer of filler material coated about the distal portion of the shaft, said filler material characterized by a dynamic viscosity;
    heating up the layer of filler material to a temperature within an operating range at which the filler material is melted or substantially plasticized, whereby the dynamic viscosity of a portion of the layer of filler material disposed close to the distal end of the shaft is lower than the dynamic viscosity of a portion of the layer of filler material disposed less close to the distal end of the shaft; and
    introducing the obturator with the distal end first into the extirpated root canal;
    wherein the layer of filler material is divided into distinct first and second portions wherein the first portion from the distal end of the shaft to an intermediate point along the distal portion of the shaft and a second portion extending from the intermediate point towards the proximal portion of the shaft, whereby the filler material in the second portion has a higher dynamic viscosity that the filler material in the first portion.

6. A method according to claim 5, wherein viscosity of the filler material in the second portion is at least 50% higher than the dynamic viscosity of the filler material in the first portion.

7. An endodontic obturator for filling an endodontically prepared root canal of a tooth, said endodontic obturator comprising:
    an elongated shaft of a flexible material, said shaft having a distal end, said shaft further having a proximal portion and a distal portion, said distal portion further comprising a tapered part;
    a layer of filler material coated about the distal portion of the shaft, said filler material characterized by a dynamic viscosity at a temperature within an operating range;
    wherein the dynamic viscosity of a portion of the layer of filler material near the distal end of the shaft is lower than the dynamic viscosity of a portion of the layer of filler material disposed towards the proximal portion of the shaft when the filler material is heated to a temperature at which substantially all the filler material is plasticized;
    wherein the layer of filler material is divided into a distinct first portion extending from the distal end of the shaft to an intermediate point along the tapered part of the shaft and a distinct second portion extending from the intermediate point towards the proximal portion of the shaft, whereby the filler material in the second portion has a higher dynamic viscosity than the filler material in the first portion.

8. An endodontic obturator according to claim 7, wherein the dynamic viscosity in the second portion is more than approximately 50% higher than the dynamic viscosity in the first portion.

9. An endodontic obturator according to claim 7, wherein the filler material of the first portion has a color which is different than the color of the filler material of the second portion.

10. An endodontic obturator according to claim 7, wherein the filler material has a composition comprising gutta-percha and/or polycaprolactone (PCL).

* * * * *

UNITED STATES PATENT AND TRADEMARK OFFICE
CERTIFICATE OF CORRECTION

PATENT NO. : 7,665,991 B1  Page 1 of 1
APPLICATION NO. : 11/439622
DATED : February 23, 2010
INVENTOR(S) : Jimmie Kert It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 270 days.

Signed and Sealed this

Twenty-eighth Day of December, 2010

David J. Kappos
*Director of the United States Patent and Trademark Office*